US008009277B2

(12) United States Patent
Chai et al.

(10) Patent No.: US 8,009,277 B2
(45) Date of Patent: Aug. 30, 2011

(54) SENSOR TECHNIQUE FOR BLACK LIQUOR OXIDATION CONTROL

(75) Inventors: Xin-Sheng Chai, Lawrenceville, GA (US); Christopher L. Verrill, Duluth, GA (US)

(73) Assignee: International Paper Company, Memphis, TN (US)

(*) Notice: Subject to any disclaimer, the term of this patent is extended or adjusted under 35 U.S.C. 154(b) by 456 days.

(21) Appl. No.: 12/290,122

(22) Filed: Oct. 27, 2008

(65) Prior Publication Data

US 2009/0122307 A1 May 14, 2009

Related U.S. Application Data

(60) Provisional application No. 61/000,474, filed on Oct. 26, 2007.

(51) Int. Cl.
*G01N 21/01* (2006.01)
*G01N 21/33* (2006.01)
*D21C 7/12* (2006.01)

(52) U.S. Cl. .......... 356/72; 356/300; 356/319; 250/373; 162/49; 162/263

(58) Field of Classification Search ........................ None
See application file for complete search history.

(56) References Cited

U.S. PATENT DOCUMENTS 4,560,440 A 12/1985 Klein et al.
4,624,742 A 11/1986 Klein et al.
4,718,979 A 1/1988 Tikka et al.
4,889,593 A 12/1989 Tikka et al.
4,988,195 A 1/1991 Doyle
5,054,920 A 10/1991 Doyle
5,242,602 A 9/1993 Richardson et al.
5,242,606 A 9/1993 Braynin et al.
5,282,931 A 2/1994 LeClerc et al.
5,364,502 A 11/1994 LeClerc et al.
5,378,320 A 1/1995 LeClerc et al.
5,582,684 A 12/1996 Holyqvist et al.
5,616,214 A 4/1997 LeClerc
5,991,029 A 11/1999 Doyle
6,023,065 A 2/2000 Garver, Jr.
7,390,669 B2 6/2008 Li et al.

(Continued)

FOREIGN PATENT DOCUMENTS

WO WO94/01769 1/1994

(Continued)

OTHER PUBLICATIONS

Hodges, et al, "Near-infrared Spectroscopy for On-line White and Black Liquor Analysis" Proceedings of the 1999 TAPPI Puling conference, (1999), p. 1097-1109.

(Continued)

*Primary Examiner* — F. L. Evans
(74) *Attorney, Agent, or Firm* — Thomas W. Barnes, III; Eric W. Guttag

(57) ABSTRACT

A method for determining simultaneously from an oxidized black liquor sample an amount of sulfide, an amount of total dissolved solids, and an amount of effective alkali present in the sample, wherein the sulfide amount, the total dissolved solids amount, and the effective alkali amount are determined by subjecting the sample to attenuated total reflection (ATR) ultraviolet/visible (UV/V) spectroscopy over a wavelength of from about 190 to about 500 nm. Data from analyzing oxidized black liquor samples, and from analyzing one or more black liquor samples which may be subjected to black oxidation, may be used in a black liquor oxidation (BLOX) system for monitoring and/or controlling sulfur emissions from a kraft process.

54 Claims, 9 Drawing Sheets

U.S. PATENT DOCUMENTS

2005/0139337 A1 6/2005 Li et al.

FOREIGN PATENT DOCUMENTS

| | | |
|---|---|---|
| WO | 0159437 | 8/2001 |
| WO | 2007006150 | 1/2007 |

OTHER PUBLICATIONS

Kester, et al, "On-Line Determination of Kraft Liquor Constituents by Fourier-Transform Near Infrared Spectroscopy", J. Pulp & Paper Sci., 30 (5):121-128 (May 2004).

Chai, et al, "Online Monitoring of Alkali, Sulfide, and Dissolved Lignin during Wood Pulping by Attenuated Total Reflection-Ultraviolet Spectroscopy and Flow Injection Techniques," Ind. Eng. Chem. Res., 42:254-258 (2003).

Chai, et al, "On-Line Analysis of EA, Sulfide and Dissolved Lignin during Kraft Pulping Process by Attenuated Total Reflection UV Spectroscopy", J. Pulp & Paper Sci., 29(6):204-207 (2003).

Chai,et al, Rapid Determination of Total Dissolved Solids in Black Liquors by ATR-UV/VIS Spectroscopy, J. Pulp & Paper Sci., 31(2):81-84 (2005).

Danielsson, Spectroscopic measurements in opaque solutions: UV-VIS spectroscopy on process liquors in the paper and pulp industries, p. 147-157, Process Control and Quality, vol. 6, 1994.

SENSOR TECHNIQUE FOR BLACK LIQUOR OXIDATION CONTROL

CROSS-REFERENCE TO RELATED APPLICATIONS AND INCORPORATION BY REFERENCE

This application claims benefit of priority to U.S. Provisional Patent Application No. 61/000,474, filed Oct. 26, 2007, which is incorporated by reference in its entirety.

FIELD OF THE INVENTION

The present invention relates broadly to a method for simultaneously measuring, residual sulfides, total dissolved solids, and effective alkali in oxidized black liquor. The present invention also broadly relates to method for black liquor oxidation control. The present invention further broadly relates to a black liquor oxidation control system.

BACKGROUND

The kraft process for pulping is the dominant method for producing pulp and paper. In the kraft process, white liquor containing the active cooking chemicals, sodium hydroxide (NaOH) and sodium sulfide ($Na_2S$), are used to cook the wood chips to separate cellulose fibers from lignin. Spent cooking chemicals and lignin are then washed away from the cellulose fibers with water, thus forming a residual spent pulping liquor stream called black liquor. Black liquor, which may initially contain up to about 20% dissolved solids (sometimes referred to as "weak" black liquor), may be concentrated in a series of multiple-effect evaporators and concentrators, for example, up to approximately 75% solids. This concentrated black liquor may then be burned, for example, in a chemical recovery furnace or boiler to recover the fuel value of the black liquor as steam, along with the inorganic chemicals as a "smelt" of sodium carbonate ($Na_2CO_3$) and sodium sulfide. (The concentrated black liquor may also be heated with steam to lower its viscosity prior to combustion in the chemical recovery furnace or boiler.) The "smelt" may then be dissolved in water to form green liquor, which may then be reacted with quick lime (CaO) to convert the sodium carbonate into sodium hydroxide to provide effective alkali ($^{-}OH$), and to thus regenerate the original white liquor.

Because black liquor contains sodium sulfide and other sulfur compounds which are malodorous, or which may form hydrogen sulfide and/or other gaseous malodorous sulfur compounds, black liquor may be subjected to oxidation prior to being burned in a chemical recovery furnace or boiler. This oxidation procedure is commonly known as black liquor oxidation or BLOX. BLOX may provide the ability to control and reduce sulfur emissions from the kraft process. The purpose of BLOX is to reduce the residual sulfide content in black liquor by oxidizing and converting the sulfides, such as sodium sulfide and/or other less stable sulfur compounds, to more stable sulfur compounds, for example, sulfates and thiosulfates, prior to contact with hot flue gases in the chemical recovery furnace or boiler. In North America, about one-third of the paper pulp mills have chemical recovery furnaces or boilers with direct contact evaporators which may require BLOX systems to treat the black liquor to reduce the level of residual sulfides. BLOX is an exothermic process, and thus results in a decrease in the heating value of the oxidized black liquor.

SUMMARY

According to a first broad aspect of the present invention, there is provided method comprising the following steps:

(a) providing spectroscopy results for one or more samples of an oxidized black liquor; and (b) determining simultaneously from the sample an amount of sulfide, an amount of total dissolved solids, and an amount of effective alkali present in the one or more samples based on the spectroscopy results of step (a), wherein spectroscopy results are based on subjecting the one or more samples to attenuated total reflection (ATR) ultraviolet/visible (UV/V) spectroscopy over a wavelength of from about 190 to about 500 nm.

According to a second broad aspect of the present invention, there is provided method comprising the following steps:

(a) providing from a black liquor oxidation system one or more samples each of: (1) oxidized black liquor; and (2) black liquor which may be subjected to black liquor oxidation;

(b) determining simultaneously for each sample an amount of sulfide, an amount of total dissolved solids, and an amount of effective alkali present in each sample based on spectroscopy results for each sample; and (c) monitoring the black liquor oxidation system based on the sulfide amount, the total dissolved solids amount, and the effective alkali amount determined in step (b), wherein the spectroscopy results are based on subjecting the one or more samples to attenuated total reflection (ATR) ultraviolet/visible (UV/V) spectroscopy over a wavelength of from about 190 to about 500 nm.

According to a third broad aspect of the present invention, there is provided a system comprising:

a black liquor stream;

at least one black liquor oxidation stage for converting at least a portion of the black liquor stream to an oxidized black liquor stream;

an attenuated total reflection (ATR) ultraviolet/visible (UV/V) spectroscopy section for determining simultaneously over a wavelength of from about 190 to about 500 nm an amount of sulfide, an amount of total dissolved solids, and an amount of effective alkali present in samples from the black liquor stream and the oxidized black liquor stream and for providing data comprising the sulfide amount, the total dissolved solids amount, and the effective alkali amount determined in the samples; and a black liquor oxidation control processor for monitoring and controlling the at least one black liquor oxidation stage based on the data provided from the attenuated total reflection (ATR) ultraviolet/visible (UV/V) spectroscopy section.

BRIEF DESCRIPTION OF THE DRAWINGS

The embodiments of the present invention will be described in conjunction with the accompanying drawings, in which.

DETAILED DESCRIPTION

Figure 1:
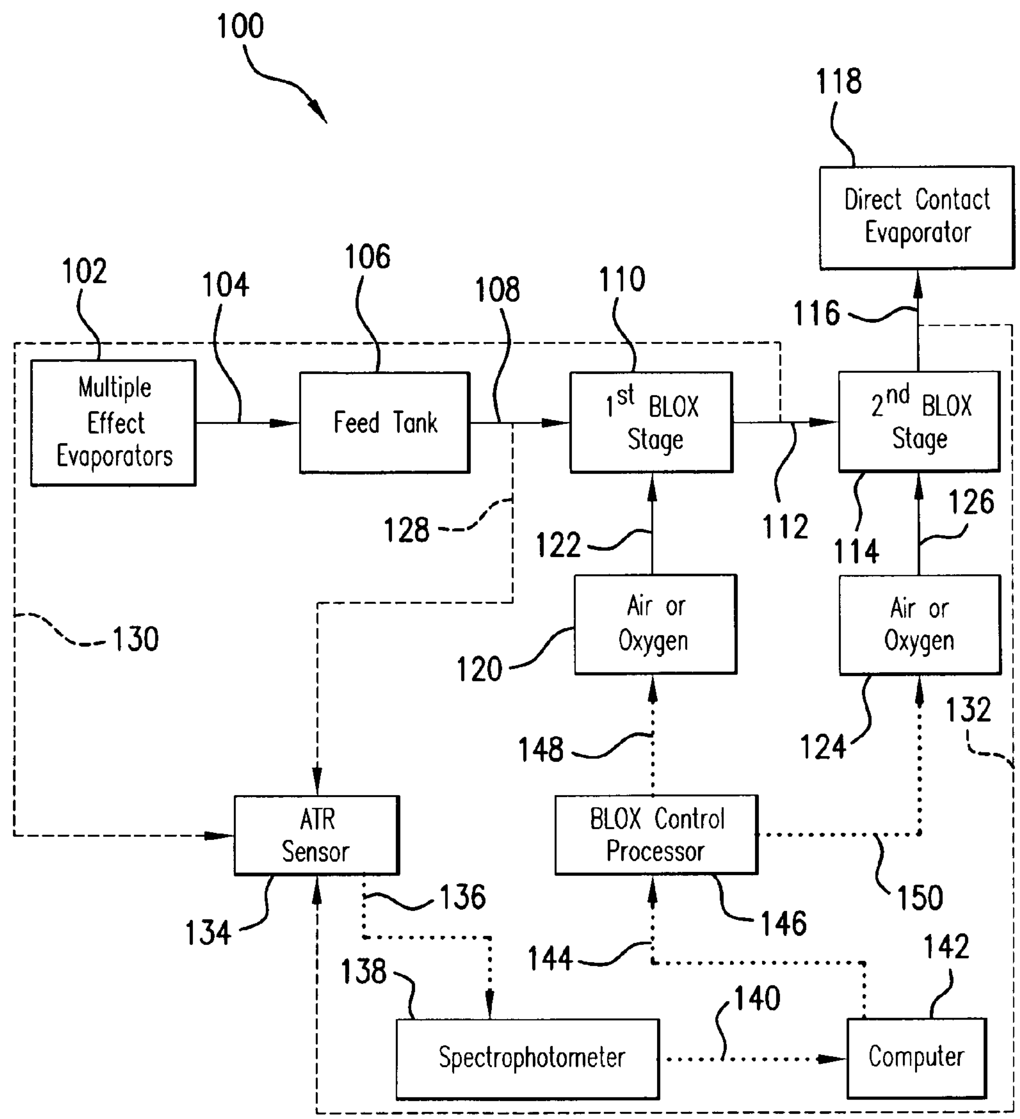
FIG. 1 is a process flow chart illustrating an embodiment of a BLOX control system according to the present invention.

It is advantageous to define several terms before describing the invention. It should be appreciated that the following definitions are used throughout this application.

Definitions

Where the definition of terms departs from the commonly used meaning of the term, applicant intends to utilize the definitions provides below, unless specifically indicated.

For the purposes of the present invention, a value or property is "based" on a particular value, property, the satisfaction of a condition, or other factor, if that value is derived by performing a mathematical calculation or logical decision using that value, property or other factor.

For the purposes of the present invention, the term "g/L" refers to grams per liter.

For the purposes of the present invention, the term "kraft liquor" refers to any aqueous stream in a kraft process which may comprise inorganic wood pulping chemicals (e.g., sodium hydroxide, sulfides, sodium carbonate, etc.), residual wood pulp components (e.g., lignin, etc.) in the case of black liquors, etc. Kraft liquors may include black liquor, oxidized black liquor, further oxidized black liquor, white liquor, green liquor, etc.

For the purposes of the present invention, the term "black liquor" refers to spent pulping liquor which is a byproduct of the kraft process during the production of paper pulp. In the kraft process, wood is decomposed into cellulose fibers (from which, for example, paper may be made), hemicellulose, lignin fragments, etc. Black liquor comprises an aqueous solution of lignin residues, hemicellulose, etc., as well as other inorganic wood pulping chemicals used in the kraft process, etc. Prior to black liquor oxidation (BLOX), black liquor may comprise a total dissolved solids level of about 50% or less (for example, about 45% or less), a residual sulfide level of at least about 13 g/L (for example, at least about 35 g/L), and an effective alkali level of at least about 6.5 g/L (for example, at least about 25 g/L).

For the purposes of the present invention, the term "black liquor oxidation (BLOX)" refers to a process for oxidizing black liquor to reduce the residual sulfide content. In BLOX, an oxygen-containing source, such as, for example, air or relatively pure oxygen (e.g., at least about 90% oxygen) is used to oxidize and convert the black liquor to oxidized black liquor. BLOX may also involve one or more oxidization stages, including oxidizing and converting oxidized black liquor to further oxidized black liquor.

For the purposes of the present invention, the term "oxidized black liquor" refers to black liquor which has been subjected to BLOX. An oxidized black liquor may comprise a total dissolved solids of up to about 70% (for example, up to about 55%, such as in the range of from about 40 to about 55%), a residual sulfide level or amount of up to about 1.7 g/L (for example, up to about 0.1 g/L), and effective alkali level or amount of up to about 50 g/L (for example, up to about 25 g/L). Oxidized black liquor may also be further oxidized and converted to a "further oxidized black liquor." A further oxidized black liquor may comprise a total dissolved solids of up to about 70% (for example, up to about 55%, such as in the range of from about 40 to about 55%), a residual sulfide level of up to about 0.2 g/L (for example, up to about 0.02 g/L), and an effective alkali level of up to about 50 g/L (for example, up to about 25 g/L).

For the purposes of the present invention, the term "white liquor" refers to an aqueous kraft liquor containing active pulp cooking chemicals. White liquor often contains sodium hydroxide and sodium sulfide, which are the two active pulp cooking chemicals. These chemicals may be present in the range of, for example, from about 65 to about 105 g/L of sodium hydroxide, and from about 26 to about 52 g/L sodium sulfide. White liquor may also contain other inactive chemicals, such as sodium carbonate in amounts of from about 22 to about 48 g/L, and small amounts of sodium sulfate, sodium chloride, and other inorganic salts.

For the purposes of the present invention, the term "green liquor" refers to a kraft liquor which is formed from the inorganic ash recovered from concentrated black liquor burned in a chemical recovery furnace where the sulfur compounds are reduced to sodium sulfide, and which are then dissolved in water to form the green liquor. Green liquor contains primarily sodium carbonate (e.g., in amounts of from about 98 to about 155 g/L), sodium sulfide (e.g., in amounts of from about 28 to about 55 g/L) and sodium hydroxide (e.g., in amounts of from about 13 to about 21 g/L). Green liquor may be converted into white liquor by contacting the green liquor with calcium hydroxide (for example, as quick lime or calcium oxide) in water. This process converts sodium carbonate ($Na_2CO_3$) into sodium hydroxide (NaOH), and is also referred to as recausticizing.

For the purposes of the present invention, the term "kraft process" (also known as the "kraft pulping or sulfate process") refers to a process for conversion of wood into wood pulp comprising cellulose fibers by treating wood chips with a mixture of active pulp cooking chemicals, such as a mixture sodium hydroxide and sodium sulfide (e.g., white liquor), to break the bonds that link lignin to the cellulose.

For the purposes of the present invention, the term "inorganic wood pulping chemicals" refers to active pulp cooking inorganic compounds used in wood pulping. Inorganic wood pulping chemicals may include hydroxides, such as sodium hydroxide, etc., which provide an effective alkali ion ($^-OH$) moiety, and sulfides, such as sodium sulfide, sodium hydrosulfide, etc., primarily as the hydrosulfide ion ($HS^-$) moiety.

For the purposes of the present invention, the term "total dissolved solids" refers to the dissolved solids in black liquor, primarily dissolved lignin, inorganic salts, and dissolved carbohydrates.

For the purposes of the present invention, the term "sulfide" refers to those sulfides which may be present in a kraft liquor, such as sodium sulfide, sodium hydrosulfide, etc., primarily as the hydrosulfide ion ($HS^-$) moiety.

For the purposes of the present invention, the term "effective alkali" refers to the hydroxide ion ($^-OH$) moiety of an alkaline compound, such a sodium hydroxide, etc.

For the purposes of the present invention, the term "attenuated total reflection (ATR)" (also known as "attenuated total reflectance") refers to a sampling technique involving the use of an ATR sensor (e.g., a transparent ATR probe) which enables samples to be examined or analyzed directly in the solid or liquid state without further preparation. ATR uses the property of total internal reflection called the evanescent wave wherein a beam of infrared light is passed through the crystal of the ATR probe in such a way that it reflects at least once off the internal surface in contact with the sample. This reflection forms the evanescent wave which extends slightly into the sample, e.g., by a few microns. The beam may then be collected by a detector (e.g., spectrophotometer) as it exits the crystal.

For the purposes of the present invention, the term "attenuated total reflection (ATR) ultraviolet/visible (UV/V) spectroscopy" (also referred to interchangeably as "ATR-UV/V spectroscopy") refers to an ATR sampling technique involving the use of an ATR sensor (e.g., a transparent ATR probe) of high refractive index ($n_p$) which is brought into contact with a sample having a lower refractive index ($n_s$), in combination with a UV/V detector, such as an UV/V spectrophotometer (e.g., a UV-8453 spectrophotometer produced by Hewlett-Packard). The ATR probe may be inserted directly into kraft liquor process component or stream (e.g., black liquor tank, reactor, process line, liquor stream, etc.) which is being sampled for analysis, may be inserted into, for example, a flow cell (sometimes called an "ATR flow cell") through which the sample to be analyzed passes, etc. Light from the spectrophotometer may be transmitted to the ATR probe via optical fibers (e.g., a fiber optic cable) and collimated before being introduced into the ATR probe at an angle, θ, to the boundary surface at the interface of the probe material and the sample. In some embodiments of the present invention, θ may be about 70° or greater. If the angle of incidence, θ, is greater than the critical angle $\theta_e$ ($\sin \theta_e$-$n_s/N_p$), total reflection will occur when the beam of light hits the boundary. In each reflection at the boundary between probe material and sample, the light penetrates a short distance into the outer medium (sample) in the form of an evanescent wave. During this short transection, light may be absorbed by the sample so that the transmitted beam carries information (data) about its spectral properties. In some embodiments, the ATR elements provide from one to three reflections of the light before exiting the probe. The light leaves the ATR probe through a lens which focuses it onto an optical fiber (e.g., a fiber optic cable) which transmits the light back to the spectrometer for spectral measurement. The optical path length may be roughly from about 1 to about 2 μm per reflection. Accordingly, ATR-UV/V spectroscopy may be used to measure very concentrated absorbing species in the solution without diluting the sample. The basic principles of ATR-UV/V spectroscopy are further explained in U.S. Pat. No. 7,390,669 (Li et al.), issued Jun. 24, 2008, the entire contents and disclosure of which are hereby incorporated by reference.

For the purpose of the present invention, the term "multivariate calibration technique" refers to a calibration technique involving observation and analysis of more than one statistical variable at a time. Multivariate calibration techniques may include Partial Least Squares (PLS) regression techniques, etc. In some embodiments, multivariate calibration set may be built from the ATR-UV/V spectra of many standard process streams having known and varying chemical concentrations. For example, black liquors with known and varying concentrations of sodium hydroxide, sodium sulfide, sodium carbonate, sodium chloride, sodium sulfate and sodium thiosulfate may be used to build a calibration set. Software may also be used in carrying out multivariate calibrations. Suitable software applications for carrying out multivariate calibrations may include Chemometrical, LabCalc, Math Lab, etc. Using these software programs, calibration files may be constructed using baseline samples with varying concentrations of the key components. For example, varying concentrations of sodium hydroxide, sodium sulfide, sodium carbonate, sodium chloride, sodium sulfate, sodium thiosulfate, etc., may be used to construct calibration files for analyzing various kraft liquor streams. The concentrations of these components may be adjusted to approximate concentrations typically found in the process stream to be analyzed and/or monitored. Other aspects of multivariate calibration are discussed further in U.S. Pat. No. 7,390,669 (Li et al.), issued Jun. 24, 2008, the entire contents and disclosure of which are hereby incorporated by reference.

For the purposes of the present invention, the term "Partial Least Squares (PLS) calibration" refers to a multivariate calibration carried out using PLS regression techniques. In some embodiments, a PLS technique of calibration may be used to reconstruct the spectrum of a mixture by adding fractions of pure component spectra and thus predict the concentrations of the interested components in the unknown sample. Once a calibration coefficient matrix is created, the concentrations of the components in the unknown sample may be determined by reconstructing the unknown spectrum from loading vectors in the calibration set. The PLS technique of calibration minimizes the effects of temperature changes, baseline shifts, component interactions in the sample, etc. Accordingly, the PLS technique may be used for quantitative determinations of component concentrations from complicated unknown ATR-UV/V spectra associated with the spectroscopic analysis of complex process streams and pulping liquors, in particular black liquors and oxidized black liquors. The basic principles of PLS techniques of calibration are further discussed in U.S. Pat. No. 7,390,669 (Li et al.), issued Jun. 24, 2008, the entire contents and disclosure of which are hereby incorporated by reference.

For the purposes of the present invention, "linear regression calibration techniques" refer to those calibration techniques which involve the relationship between one or more independent variables and another variable, called a dependent variable, is modeled by a least squares function, called linear regression equation. Linear regression calibration techniques may be useful to determine component concentrations if the total concentration of all major components, or at least some of those components, of the kraft process stream do not change significantly. For example, as applied to kraft liquor streams, linear regression calibration techniques may be used if the total dissolved solids concentration, e.g., sodium hydroxide, sodium carbonate and sodium sulfide, does not change significantly. Significant fluctuations in concentration may affect the refractory index of the kraft liquor resulting in a non-linear relationship between absorbency value and concentration. If the processing stream experiences large fluctuations in concentration, the refractory index change of the kraft liquors may cause the absorbency value to become non-linear, corresponding to the component concentrations and thus a multivariate calibration technique may be required for the calibration under such conditions. For example, if the fluctuations exceed about 5%, then linear regression calibration techniques may not be useful. Linear regression under appropriate circumstances may be desirable since this calibration technique may be simpler to carry out. Linear regression calibration techniques may be desirable because of simpler calculations, and because fewer standard solutions may be necessary to build a base set file. The basic principles of linear regression calibration techniques are further discussed in U.S. Pat. No. 7,390,669 (Li et al.), issued Jun. 24, 2008, the entire contents and disclosure of which are hereby incorporated by reference.

For the purposes of the present invention, the term "empirical calibration technique" refers to a calibration technique involving a simple linear regression based on, for example, spectral signals at 2 to 4 given wavelengths.

For the purposes of the present invention, the term "controlling the black liquor oxidation system" refers to controlling the degree of oxidation of the black liquor (or oxidized black liquor) streams, including metering, regulating, etc., the flow, amount, etc., of the oxygen-containing source used in oxidizing the black liquor (or oxidized black liquor) streams, monitoring, measuring, analyzing, determining, etc., the components present in the black liquor and oxidized black liquor streams, etc.

For the purposes of the present invention, the term "processor" refers to a device, equipment, machine, apparatus, controller, etc., as well as combinations thereof, which is capable of, for example, executing instructions, implementing logic, analyzing, calculating and storing values and data, controlling process equipment, components, etc. Exemplary processors may include application specific integrated circuits (ASIC), central processing units (CPU), microprocessors, such as, for example, microprocessors commercially available from Intel and AMD, computers, distributed control systems (DSC), programmed/programmable logic controllers (PLC), a proportional integral derivative (PID) controller, programmable automation controllers (PAC), etc., as well as combinations of such processors.

Description

New BLOX technologies have been introduced in recent years that are based on the use of molecular oxygen instead of air. These new BLOX processes may offer the advantages of smaller equipment size and prevent the release of vent gases (unreacted nitrogen from air), but there remains a lack of understanding of the mechanisms controlling the relative rates of sulfide (desirable) and organic (undesirable) oxidation. Under-oxidation may result in incomplete oxidation and conversion of sulfide ($HS^-$ ion) in the black liquor to the more stable (and less troublesome from a sulfur emissions standpoint) thiosulfate form, with the residual sulfide causing undesired total reduced sulfur (TRS) emissions and sulfur chemical loss. Conversely, over-oxidation may consume more effective alkali ($OH^-$ ion) in the black liquor, which may lead to organic (e.g., lignin) precipitation and equipment fouling. Excessive oxidation of organics may also result in unwanted loss of black liquor fuel value.

Therefore, on-line analysis of the sulfide content in the black liquor (as well as the oxidized black liquor) may be important in the development of a monitoring and/or control system for high sulfide selectivity in the BLOX process. Retention of from about 1 to about 2% of black liquor heating value by better control of oxidation may also improve chemical recovery furnace or boiler efficiency for steam and power generation with resulting fossil fuel savings. In other words, monitoring and controlling the BLOX process may provide a balance of reduced residual sulfides, without significantly reducing organics which provide improved energy benefits. However, the harsh conditions of elevated temperature (e.g., from about 100° to about 140° C.) and relatively high total dissolved solids content (for example, from about 40 to about 55%) make conventional analytical methods difficult to apply for on-line monitoring of kraft mill operations.

A commercial sensor system for sulfide detection in oxidized black liquor is made by Southwell Controls Ltd. See BLOX (Black Liquor Oxidation Sensor: at http://www.southwellcontrols.com/blox.cfm. This electrochemical-based sensor may be limited to a low range of sulfide detection (from 0.05-2.0 g/L sodium sulfide) and may also be sensitive to the changes in the liquor organics (i.e., hardwood and softwood). Thus, frequent calibration may be required for a kraft process where the wood species change. This may make such a BLOX sensor impractical for industrial application. Optical sensor technologies based on near infrared (NIR) spectroscopy have also been used for composition analysis of kraft liquors. See Hodges et al. "Near-infrared Spectroscopy for On-line White and Black Liquor Analysis," *Proceedings of the* 1999 *TAPPI Pulping Conference*, (1999), p. 1097; Kester, et al., "On-Line Determination of Kraft Liquor Constituents by Fourier-Transform Near Infrared Spectroscopy," *J. Pulp & Paper Sci.,* 30(5):121-128 (May, 2004). However, these technologies may not be suitable for detecting lower sulfide contents in black liquor because both IR and NIR are relatively insensitive to lower sulfide concentrations.

Previously, an attenuated total reflection (ATR) UV spectroscopic technique was used for simultaneous determination of effective alkali (OH-ion), sulfide (HS-ion) and dissolved lignin in black liquors for both batch and continuous kraft processes. See Chai, et al., "Online Monitoring of Alkali, Sulfide, and Dissolved Lignin during Woof Pulping by Attenuated Total Reflection-Ultraviolet Spectroscopy and Flow Injection Techniques," *Ind. Eng. Chem. Res.,* 42:254-258 (2003); Chai, et al., "On-Line Analysis of EA, Sulfide And Dissolved Lignin during Kraft Pulping Process by Attenuated Total Reflection UV Spectroscopy," *J Pulp & Paper Sci.,* 29(6):204-207 (2003. More recently, the applicability of ATR-UV spectroscopy for determination of total dissolved solids content in weak and strong black liquor has been demonstrated. See Chai, et al., "Rapid Determination of Total Dissolved Solids in Black Liquors by ATR-UV/VIS Spectroscopy," *J. Pulp & Paper Sci.,* 31(2):81-84 (2005).

A major advantage of UV spectroscopy over NIR is its proportional response to the absorbed species and its high sensitivity to the sulfide species, which makes the measurement more reliable and accurate. Combined with an ATR technique, ATR-UV spectroscopy allows one sensor to directly measure several species of interest in the concentrated process liquors without need significant dilution; thus minimizing unwanted sulfide oxidation by dissolved oxygen in the diluent stream. This opens up the possibility for the determination of low levels of residual sulfide in kraft liquors have a complicated compositional matrix (such as oxidized black liquor) which.

In some embodiments, the present invention provides a method for simultaneously measuring, residual sulfides, total dissolved solids, and effective alkali in oxidized black liquor using an attenuated total reflection (ATR) ultraviolet (UV)/visible (V) sensor technique. In these embodiments, attenuated total reflection (ATR) ultraviolet (UV)/visible (V) sensor technique (ATR-UV/V spectroscopy) is used to simultaneously determine sulfide, total dissolved solid and effective alkali in oxidized black liquor a wavelength range of from about 190 to about 500 nm (e.g., in the range of from about 190 to about 450 nm). Because of the higher concentration total dissolved solids (for example, up to about 70%, e.g., up to about 55%, such as in the range of from about 40 to about 55%), and especially the lower concentration of residual sulfides (e.g., about 1.7 g/L or less, such as about 0.1 g/L or less), in oxidized black liquors, the simultaneous determination of the amount of residual sulfides, the amount of total dissolved solids (primarily dissolved lignin), and the amount of effective alkali in such oxidized black liquors may be a significantly greater challenge, especially in providing spectral information in the wavelength range of from about 300 to about 450 nm (or higher) for improving sensitivity in residual sulfide detection. ATR-UV/V spectroscopy provides a useful and accurate technique for the simultaneous determination of the amount of residual sulfides, the amount of total dissolved solids (primarily dissolved lignin), and the amount of effective alkali in such oxidized black liquors.

In some embodiments of the present invention, an attenuated total reflection (ATR) ultraviolet (UV)/visible (V) sensor technique may be used for black liquor oxidation control. Using an empirical calibration technique or a partial least squares (PLS) multivariate calibration technique, and multi-wavelength ATR-UV/V spectral signals in a wavelength range of from about 190 to about 500 nm (e.g., in the range of from about 190 to about 450 nm) for oxidized black liquor measurements (as well as measurements for black liquor which may be oxidized and converted to oxidized black liquor), simultaneous determination of the amount of sulfide, the amount of total dissolved solids and the amount of effective alkali may be achieved in oxidized black liquor (as well as black liquor which may be oxidized and converted to oxidized black liquor) for monitoring and controlling a BLOX system. This technique may also be used as an on-line tool for monitoring and controlling BLOX systems.

In some embodiments, the present invention provides a black liquor oxidation (BLOX) control system which comprises at least one black liquor oxidation stage for converting at least a portion of a black liquor stream to an oxidized black liquor stream. This BLOX system includes an attenuated total reflection (ATR) ultraviolet/visible (UV/V) spectroscopy section for determining simultaneously over a wavelength of from about 190 to about 500 nm an amount of sulfide, an amount of total dissolved solids, and an amount of effective alkali present in samples taken from the black liquor stream and the oxidized black liquor stream and for providing data comprising the sulfide amount, the total dissolved solids amount, and the effective alkali amount determined in the samples. This BLOX system also includes a black liquor oxidation control processor for monitoring and controlling black liquor oxidation in the at least one stage based on the sulfide amount, the total dissolved solids amount, and the effective alkali amount data provided by the attenuated total reflection (ATR) ultraviolet/visible (UV/V) spectroscopy section.

FIG. 1 provides a process flow chart which illustrates an embodiment of a BLOX control system according to the present invention, indicated generally as 100. As shown in FIG. 1, BLOX control system 100 may include multiple effect evaporators, indicated as 102, which initially concentrate the sources of black liquor from a kraft process. The concentrated black liquor from evaporators 102 may be collected, as indicated by arrow 104, in a feed tank, indicated as 106. At least portion, up to all, of the collected black liquor in feed tank 106 may then be fed as a black liquor feed stream, indicated by arrow 108, to a first black liquor oxidation (BLOX) stage, indicated as 110. At least portion, up to all, of the oxidized black liquor from first BLOX stage 110 may then be fed as an oxidized black liquor stream, indicated by arrow 112, to a second black liquor oxidation (BLOX) stage, indicated as 114. At least portion, up to all, of the further oxidized black liquor resulting from second BLOX stage 114 may then be fed as a further oxidized black liquor stream, indicated by arrow 116, to a direct contact evaporator, indicated as 118, which may, for example, contact stream 116 with hot flue gases and/or remove water from stream 116 to achieve a higher dissolved solids concentration of, for example, up to 70% (e.g., from about 62 to about 70%) before being supplied to, for example, a chemical recovery furnace or boiler. As further shown in FIG. 1, a first oxygen-containing source 120 supplies a source of oxygen (e.g., air, oxygen, etc.), as indicated by arrow 122, to first BLOX stage 110 for oxidizing and converting at least a portion of black liquor feed stream 108 to oxidized black liquor stream 112. Similarly, a second oxygen-containing source 124 supplies a source of oxygen (e.g., air, oxygen, etc.), as indicated by arrow 126, to second BLOX stage 114 for oxidizing and converting at least a portion of oxidized black liquor stream 112 to further oxidized black liquor stream 116.

As shown in FIG. 1, one or more samples (e.g., a plurality of samples) of black liquor may taken from black liquor feed stream 108. Similarly, one or more samples (e.g., a plurality of samples) of oxidized black liquor may be taken from oxidized black liquor feed stream 112, as well as one or more samples (e.g., a plurality of samples) from further oxidized black liquor stream 116. As shown in FIG. 1, respectively, by dashed arrows 128, 130, and 132, the one or more samples of black liquor taken from feed stream 108, the one or more samples of oxidized black liquor taken from feed stream 112, and the one or more samples of further oxidized black liquor taken from feed stream 116 may be analyzed to determine the amount of sulfide, the amount of total dissolved solids, and the amount of effective alkali present in each of these samples by using an ATR sensor (e.g., ATR probe), indicated generally as 134. Light leaving the ATR sensor 134 may then be transmitted (e.g., via a fiber optic cable), as indicated by dotted arrow 136, to a spectrophotometer, indicated as 138. Spectrophotometer 138 generates or provides an absorbency spectrum (in the form of spectral data) over the analyzed wavelength range, e.g., from about 190 to about 500 nm.

The spectral data generated or provided by spectrophotometer 138 may then be transmitted, as indicated by dotted arrow 140, to a spectral data analyzer in the form of, for example, a computer, indicated as 142, from which the amount of residual sulfides, the amount of total dissolved solids, and the amount of effective alkali present in the sample may be determined, for example, by using a multivariate calibration and/or linear regression calibration technique. (Computer 142, spectrophotometer 138 and ATR sensor 134, together, may comprise the ATR-UV/V spectroscopy section of system 100.) The amount of residual sulfides, the amount of total dissolved solids, and the amount of effective alkali present in the analyzed sample, as determined by computer 142, may then be inputted, as indicated by dotted arrow 144, to a BLOX control processor, as indicated by 146. (In some embodiments, computer 142 and BLOX control processor 146, may be part of the same unit or component of system 100, or may be separate units or components of system 100.) Based on the data inputted from computer 142, BLOX control processor 146 may send one or more signals, as indicated by dotted arrow 148, to first oxygen-containing source 120 to regulate, control, etc., the degree of oxidization of black liquor feed stream 108 in first BLOX stage 110. Similarly, BLOX control processor 146 may send one or more signals, as indicated by dotted arrow 150, to second oxygen-containing source 124 to regulate, control, etc., the degree of further oxidization of the oxidized black liquor feed stream 112 in second BLOX stage 114.

Figure 2:
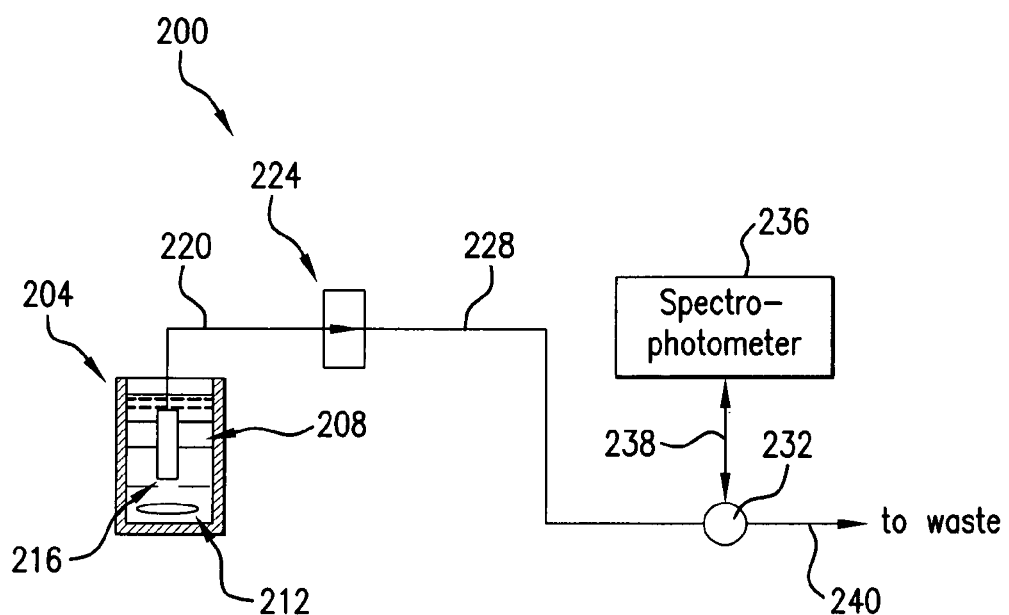
FIG. 2 is a process flow diagram of an embodiment of a flow analysis ATR-UV/V section which may be useful in carrying out embodiments of the present invention.

An embodiment of a flow analysis ATR-UV/V section which may be useful in carrying out embodiments of ATR-UV/V spectroscopy, as well as BLOX control, according to the present invention is illustrated in FIG. 2 by a schematic diagram of a flow analysis ATR-UV/V section, indicated generally as 200. As shown in FIG. 2, flow analysis ATR-UV/V section 200 includes an analysis container 204 (e.g., a beaker) which contains a sample 208 of black liquor (or oxidized black liquor) to be analyzed for the respective amounts of sulfide, total dissolved solids, and effective alkali present in sample 208. Sample 208 is stirred by stirrer 212 (e.g., a magnetic stir bar). Sample 208 passes through screen 216 which filters sample 208 to remove solid particles as sample 208 is pumped from container 204. Filtered sample stream 220 is pumped from container 204 and through screen 216 by pump 224 (e.g., a peristaltic pump). ATR flow cell liquor stream 228 goes from pump 224 to Attenuated Total Reflectance (ATR) flow cell 232 (which also functions as the ATR sensor). ATR flow cell 232 is connected to spectrophotometer 236 (for example, by fiber optic cable). Light from the spectrophotometer 236, as indicated by double headed arrow 238, passes through ATR flow cell 232 where some light is absorbed by ATR flow cell liquor stream 228. The light which leaves ATR flow cell 232 (for example, via the fiber optic cable) is returned, as also indicated by double headed arrow 238, to spectrophotometer 236 which spectrally analyzes the returned light. Spectrally analyzed ATR flow cell liquor stream 228 may be disposed of as a waste stream 240. Spectrophotometer 236 generates a UV/V absorbency spectrum (in the form of spectral data) of ATR flow cell liquor stream 228 over a predetermined range of wavelength of, for example, from about 190 to about 500 nm (e.g., from about 190 to about 450 nm), which may be recorded by a computer (not shown). The spectral data generated or provided by spectrophotometer may then be analyzed, for example, by using either a multivariate calibration program and/or linear regression calibration program installed on a spectral data analyzer (e.g., a computer) which determines the concentration of the individual chemical components (i.e., the respective amounts of sulfide, total dissolved solids, and effective alkali.) from the spectral data.

FIG. 2 illustrates the principle of a flow analysis ATR-UV/V section on a “bench scale.” For some embodiments of a BLOX control system, ATR flow cell liquor stream 228 may be obtained directly from the black liquor and oxidized black liquor streams and may then be passed directly through an ATR flow cell 232. Prior to reaching ATR flow cell 232, ATR flow cell liquor stream 228 may be cooled, for example, by being passed through a cooling coil, heat exchanger, etc., to reduce the temperature of stream 228 to, for example, in the range of from about 25° to about 70° C. (e.g., from about 50° to about 70° C.). Each determination of the respective amounts of sulfide, total dissolved solids, and effective alkali may be carried out within a defined temperature range to minimize deviations which may be occasioned by temperature differences. For example, each determination may be carried out at a temperature which varies by no more than about ±5° C. (e.g., by no more than about ±1° C.). ATR flow cell 232 may also be purged periodically to remove residues which may be present therein. These purged residues may be returned to the BLOX control system for further processing.

EXAMPLES

Various experiments illustrating the use of ATR-UV spectroscopy in measuring the respective amounts of residual sulfides, total dissolved solids, and effective alkali in black various liquors from a BLOX control system are described as follows.

Black Liquor Samples

Black liquor samples are taken from three different locations, i.e., the feed tank (see dashed arrow 128 in FIG. 1), after the first stage BLOX stage (see dashed arrow 130 in FIG. 1), and after the second BLOX stage (see dashed arrow 130 in FIG. 1), from a BLOX control system (see system 100 of FIG. 1), in which the total dissolved solids content may vary in the range of from about 40 to about 55%. Each sample is cooled down to room temperature (e.g., at 25° C.) (or some other fixed temperature) after passing through a cooling coil submerged in running tap water.

Apparatus, Sample Preparation, and Measurement

All measurements may be conducted in a laboratory flow analysis ATR-UV/V section, as illustrated in FIG. 2 and as previously described. A UV/V spectrophotometer 236 is able to perform absorption measurements to cover a wavelength range of from about 190 to about 450 nm or higher. A black liquor (or oxidized black liquor) sample is poured into a beaker 204, and weighed by a balance. Then, a double weight of water is added to dilute sample 208 (because of the thickness/viscosity of the original sample at room temperature so that it is able to flow). This diluted sample 208 is mixed by magnetic stirring (e.g., with a magnetic stir bar 212) and is pumped through screen 216 by a peristaltic pump 224 to ATR flow cell 232 for absorption measurements by UV/V spectrophotometer 236, with the resulting data being recorded by a computer using Chemstation software (Agilent, Inc).

Calibrations

Numerous fresh samples from different locations in a BLOX system (e.g., such as system 100 of FIG. 1) are collected. The residual amounts of sulfide, total dissolved solids and effective alkali present in these kraft liquors are analyzed by the reference methods known in the art. Both linear and multivariate calibration techniques are also used to build up a correlation between the ATR-UV signal data, and the data obtained by these reference methods.

Spectral Characterizations of the Oxidized Black Liquor

1. Black Liquor

Figure 3:
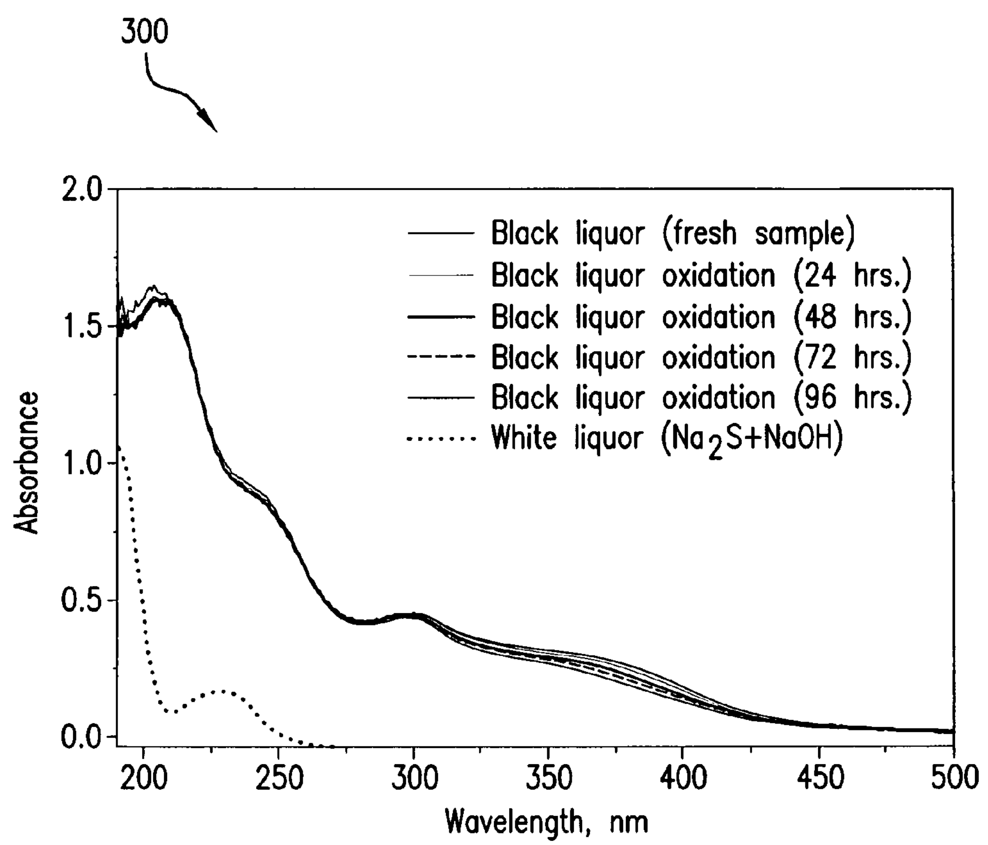
FIG. 3 is a graphical plot of spectral responses during progressive oxidation of a dilute black liquor sample.

FIG. 3 is a graphical plot, generally indicated as 300, which shows the spectral characterizations of a set of black liquors measured by ATR-UV/V spectroscopy which have been subjected to oxidation by air at room temperature for varying time periods. It can be seen in plot 300 of FIG. 3 that dissolved lignin in black liquor, as well as in oxidized black liquor, is the major species that has a strong absorption covering the whole UV and part of the visible (V) wavelength range (190 to 450 nm). For comparison, a spectrum of white liquor which contains mainly sulfide (as $HS^-$) and effective alkali (as $OH^-$) is also included in plot 300 of FIG. 3. As shown in plot 3 of FIG. 3, there are two absorption peaks in white liquor which are located around the wavelength of 197 nm for the effective alkali and the wavelength of 230 nm for the sulfide, respectively. Accordingly, the absorptions contributed by the residual sulfide and the effective alkali in black liquor overlap with the lignin spectrum.

As further shown in plot 300 of FIG. 3, the spectral changes in the black liquors take place during a slow oxidation (by air) at a room temperature to provide progressively oxidized black liquors, which decreases the absorption at the wavelengths around 232 nm and 370 nm, as also shown by plot 300. It is understandable that the absorption decrease around 230 nm is caused by sulfide oxidation, which is converted to thiosulfate (or other stable sulfur compounds such as polysulfide). It is believed that the absorption decrease around 370 nm is caused by a structure change in the dissolved lignin (i.e., by oxidation eliminating some of the functional groups, such as the methoxy groups, bound on the benzene ring of lignin, thus causing lignin absorption to decrease at this wavelength range). If the dissolved lignin undergoes oxidation, the lignin molecules may be modified and spectral characterization changes at higher UV wavelengths may be recognized. This provides indirect information about the extent of black liquor oxidation, which may be helpful for black liquor monitoring (and for oxidation control) during oxidation thereof.

It is also observed that the oxidation of black liquor may lead to methanol formation, e.g., due to demethoxylation of lignin, which may result in a decrease in effective alkali concentration in the oxidized black liquor.

2. BLOX Liquors

Figure 4:
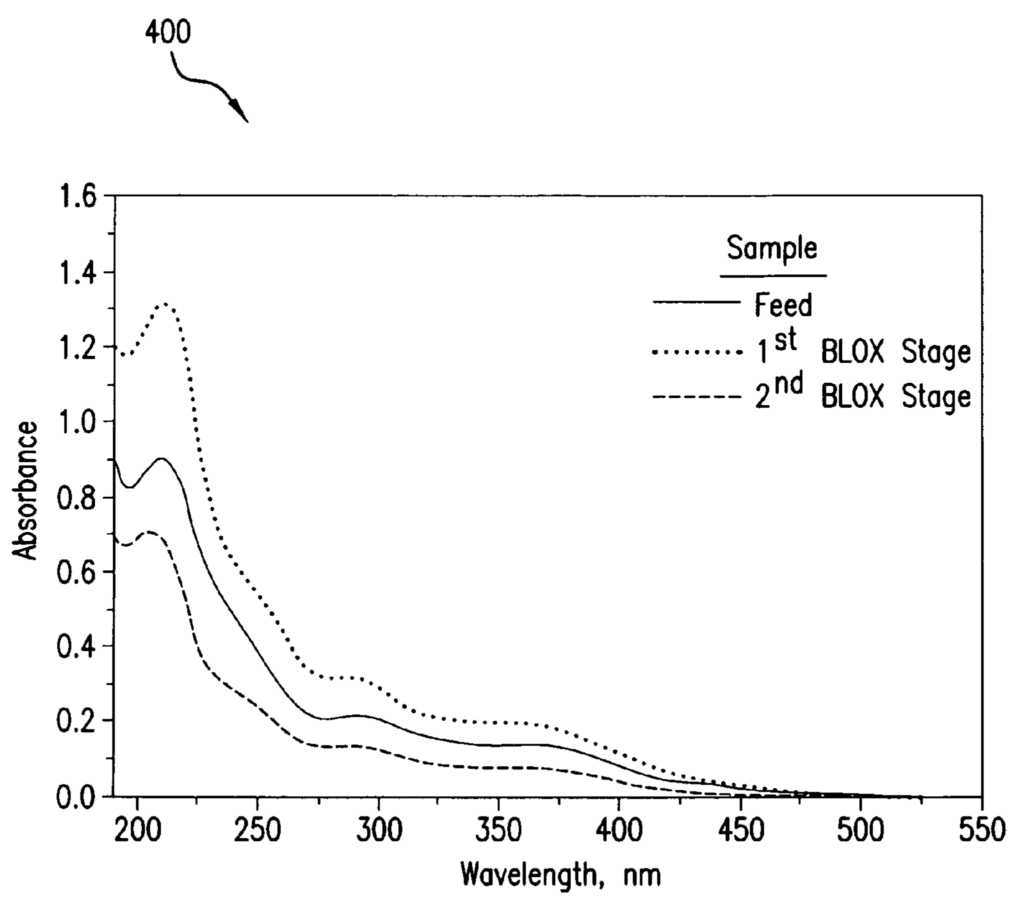
FIG. 4 is a graphical plot of the original spectra of black liquors taken from three different locations in a BLOX process.
Figure 5:
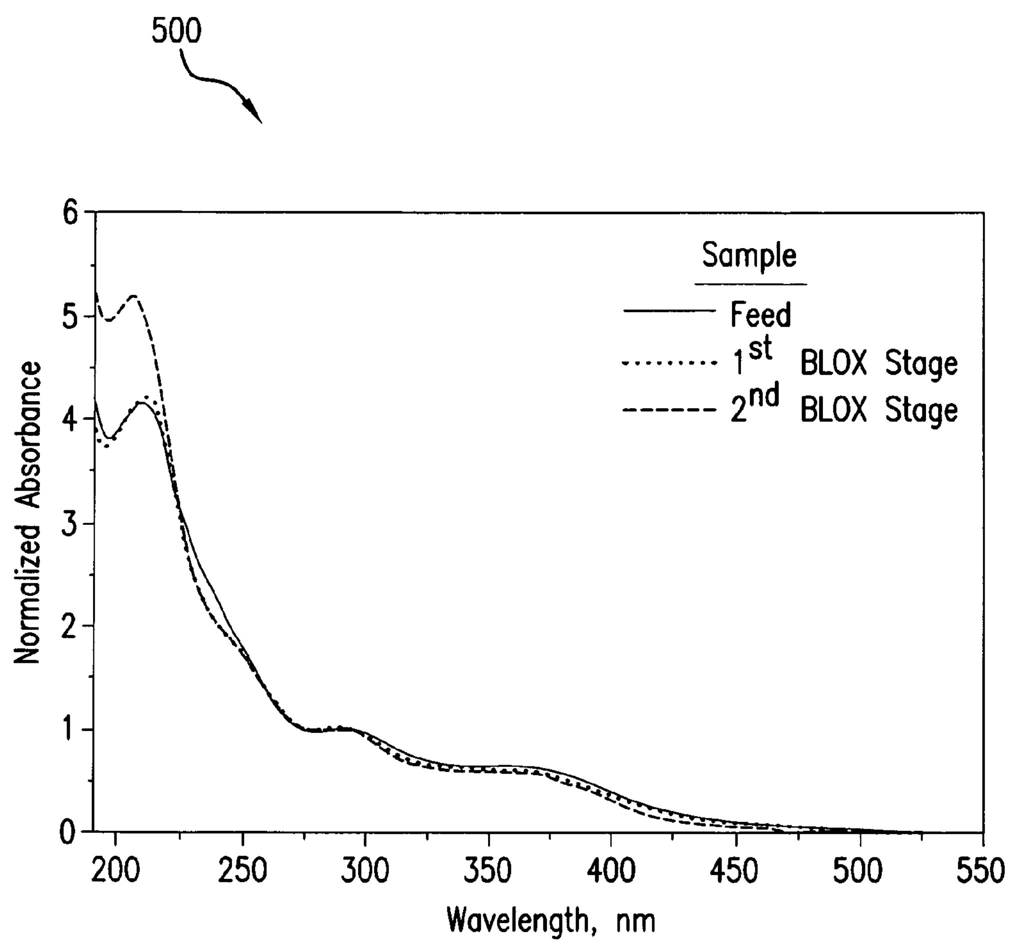
FIG. 5 is a graphical plot of the normalized spectra of the three black liquors of FIG. 1.

FIG. 4 is a graphical plot, generally indicated as 400, which shows the spectra of black liquors and oxidized black liquors withdrawn from three different locations identified as Feed, $1^{st}$ Stage BLOX, and $2^{nd}$ Stage BLOX (see, respectively, dashed arrows 128, 130, and 132 in FIG. 1) in an operating BLOX process at a kraft process site. The total dissolved solid contents in these black liquors may vary in the range of from about 40 to about 55%. For comparison, the spectra from these black liquor samples may be normalized using 280 nm as a reference wavelength, which sets the total dissolved solids content at the same level. Basically, the absorption at 280 nm may be regarded as the contribution from only the dissolved lignin. FIG. 5 is a graphical plot, indicated generally as 500, of the normalized spectra which shows that, within a short residence (reaction) time in the BLOX process, the change in the spectral characterizations of these kraft liquors (like FIG. 4, identified as Feed, $1^{st}$ Stage BLOX, and $2^{nd}$ Stage BLOX) may be more significant, especially for the absorption around 230 nm (sulfide), than that caused by air oxidation as shown in plot 300 of FIG. 3. The absorptions at the wavelengths above 260 nm are basically contributed by the dissolved lignin. However, the non-absorption species such as sulfide, effective alkali, as well as other inorganic and organic species, also have an effect on the absorption at the wavelengths above 260 nm (in terms of the refractive index), which provides an opportunity to determine the total dissolved solids based on the lignin absorption data. See Chai, et al., "On-Line Analysis of EA, Sulfide And Dissolved Lignin during Kraft Pulping Process by Attenuated Total Reflection UV Spectroscopy," *J Pulp & Paper Sci.,* 29(6):204-207 (2003).

Oxygen Effect on Sulfide Measurement

Figure 6:
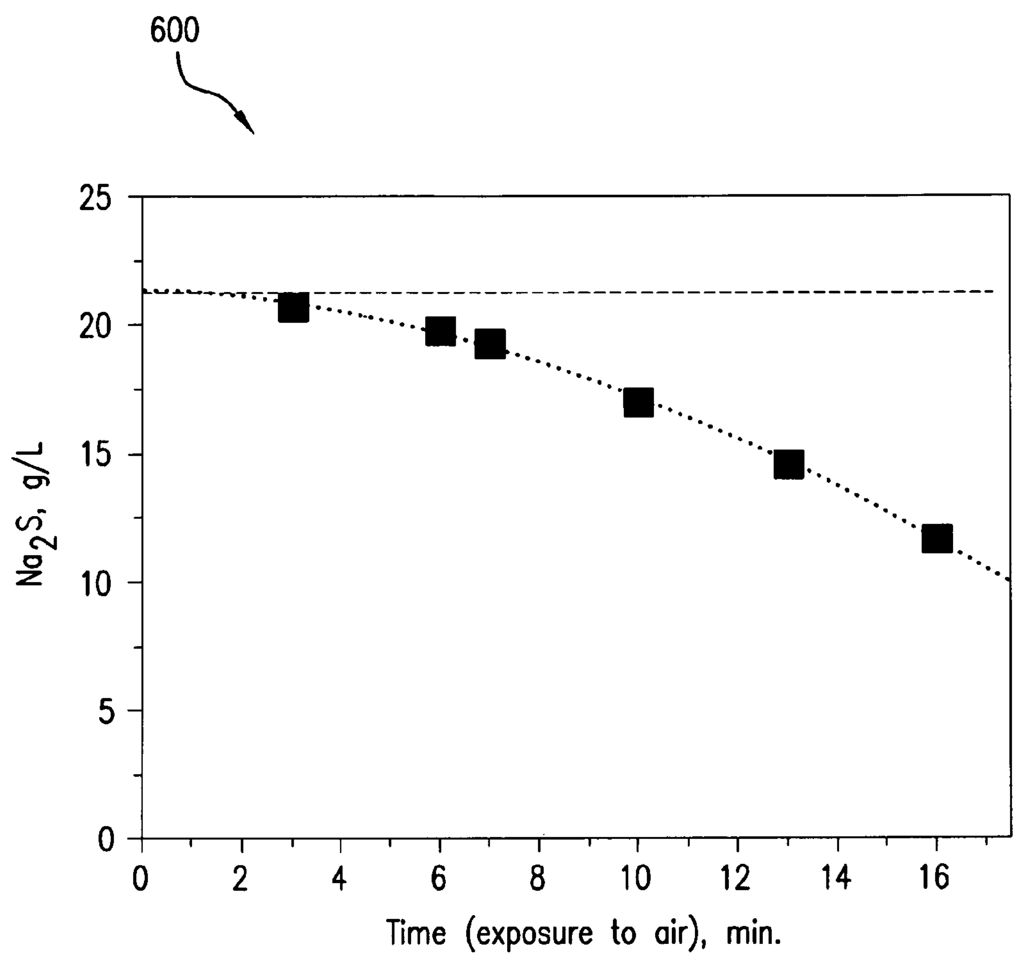
FIG. 6 is a graphical plot showing the effect of oxygen (in air) on the sulfide measurement in oxidized black liquors.

Sulfide may be easily oxidized by dissolved oxygen. As shown in the graphical plot, indicated generally as 600, of FIG. 6, a rapid oxidation of sulfide may take place when the black liquor is exposed to air. (The horizontal dashed line in FIG. 6 represents the base line where there is no reaction of sulfide with the dissolved oxygen.) Therefore, a particular measure may be taken to minimize the oxygen effect. In this experiment, a $CO_2$-free distilled water may be used as a diluent in the sample preparation. The sample container may be covered with a film to isolate air from the solution during the measurement.

Determination of Major Species in the BLOX System Liquors

In UV/V spectroscopy, the spectral absorption of a given species is proportional to its concentration in the solution, which provides a basis for developing a reliable sensor technique to quantify these species in the process liquor. Calibration may be important in many of these instrument based analytical techniques. In this experiment, both linear and multivariate calibrations are developed.

1. Linear Calibration Technique a. Determination of Total Dissolved Solids (TDS)

Figure 7:
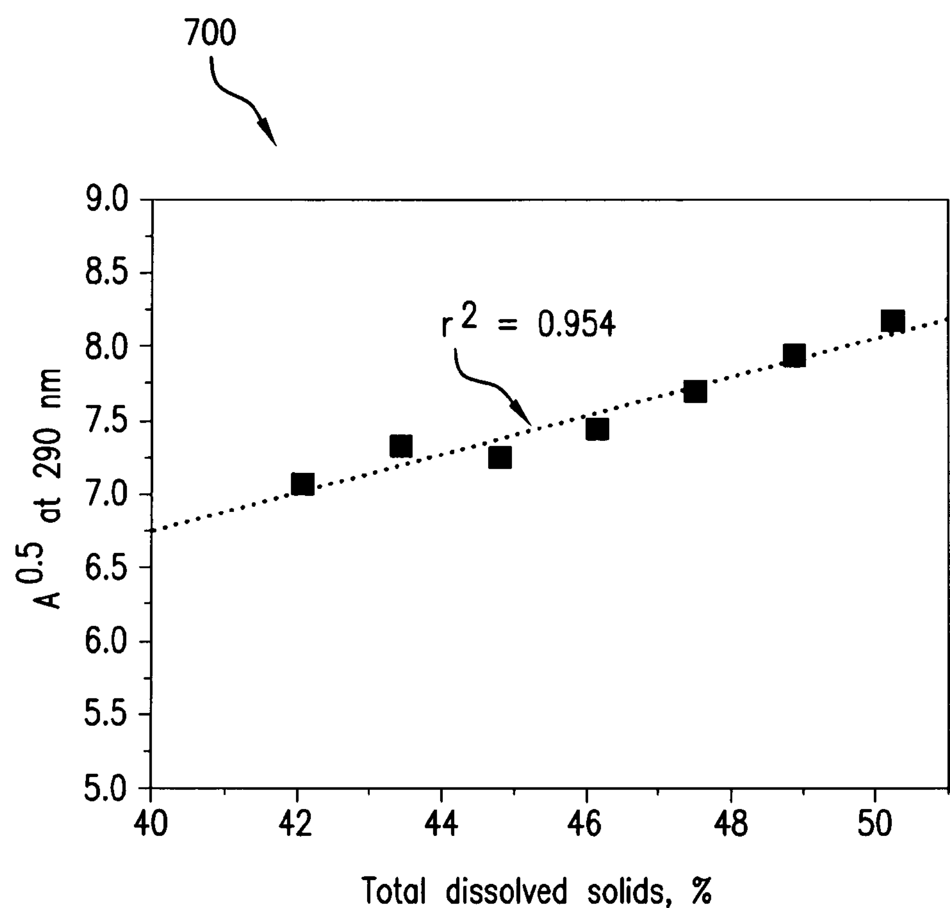
FIG. 7 is a graphical plot showing the relationship between the square root of absorbance (at 290 nm) and total dissolved solids in various oxidized black liquors.

A linear relationship is found between the square root of the UV absorption at 290 nm and the amount of total dissolved solids for the weak black liquor. FIG. 7 is as graphical plot, indicated generally as 700, which shows such a linear relationship exists in the oxidized black liquor over the total dissolved solids range of from about 42 to about 50%.

The percentage of total dissolved solids (% TDS) may be calculated according to the following Equation 1:

$$\%TDS=k\sqrt{A_{290}}-b \quad (1)$$

wherein the value of the slope (k) and intercept (b) are, for example, 172.3 and 63.4, respectively, in the present measurement.

b. Determination of the Residual Sulfide

As discussed above, the sulfide absorption peak is around 230 nm, which overlaps completely with that of absorption spectrum for dissolved lignin. Thus, by subtracting the absorption contributed by the dissolved lignin from total absorption at a given wavelength, the absorption contributed by the sulfide may be calculated, which is proportional to the concentration of the sulfide in the oxidized black liquor (or black liquor which may be oxidized and converted to oxidized black liquor).

Figure 8:
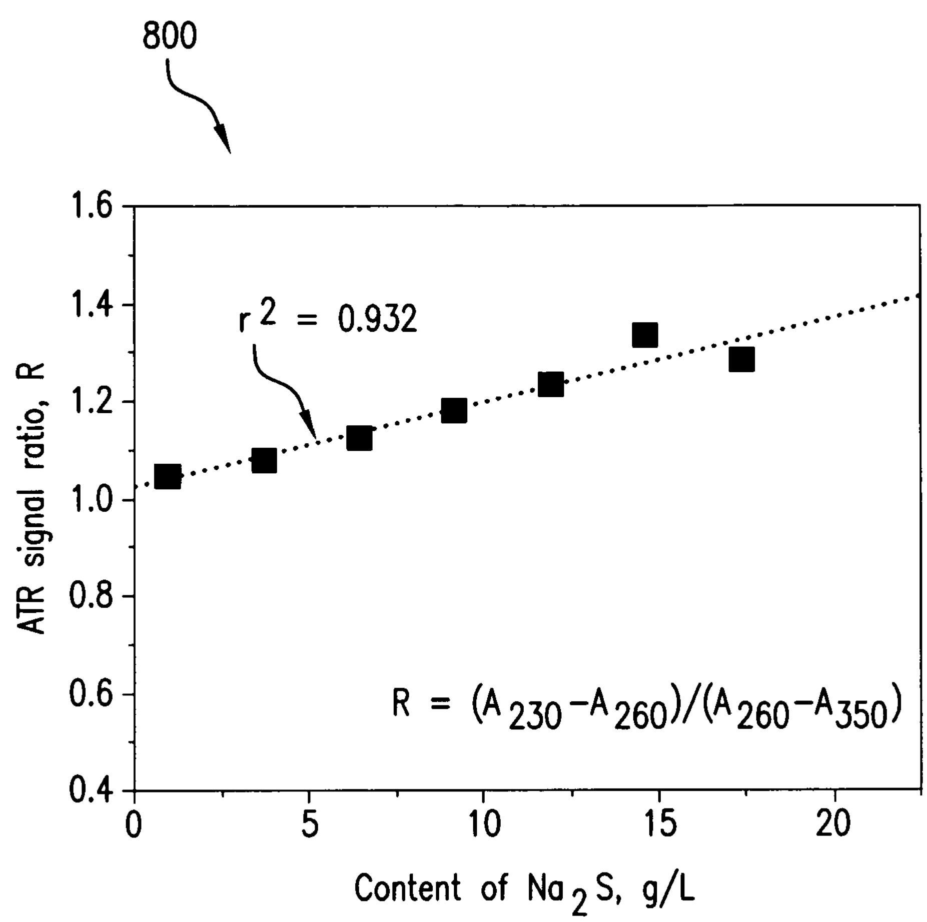
FIG. 8 is a graphical plot of the ATR sensor signal ratio vs. sulfide content in various oxidized black liquors.

Since the structure of the dissolved lignin might be affected in these oxidized black liquors, and a possible spectrum shifting may also occur, the absorption at 260 nm is introduced as a relative reference to improve the reliability for the sulfide measurement. FIG. 8 is a graphical plot, indicated generally as 800, which shows a linear relationship between the ratio (R) and sulfide content in oxidized black liquors.

The amount of sulfide based on the spectroscopic measurement may be calculated according to the following Equation 2:

$$[Na_2S]=a*R-b \quad (2)$$

wherein $$R_{Na_2S}=\frac{A_{230}-A_{260}}{A_{260}-A_{350}},$$

with the values of the slope (a) and the intercept (b) being, for example, 54.3 and −95.5, respectively, in the present measurement.

c. Determination of the Residual Effective Alkali (REA)

Similar to the sulfide amount determination, a linear relationship may also be found based on the designated ratio, i.e., $$R_{REA}=\frac{A_{215}-A_{200}}{A_{290}-A_{320}},$$

and the residual effective alkali (REA) concentration in the oxidized black liquors. The REA concentration may be calculated according to following Equation 3:

$$[REA]=a*R^2-b \quad (3)$$

wherein the values of the slope (a) and intercept (b) are, for example, 2 and 0.65, respectively, in the present measurement.

It should be noted that the value of the slope (a) and intercept (b) may be different in Equation 3 in different systems, which is also true of slope (a) and intercept (b) in Equation 2, and slope (k) and intercept (b) in Equation 1.

2. Multivariate Calibration Methods

Multivariate data calibration analysis techniques may be useful for the evaluation of experimental data. See Hoskuldsson, "PLS Regression methods," *J Chemometrics,* 2:211 (1988). In particular, multivariate data calibration analysis has been found to be useful for ATR-UV/V spectroscopy when selectivity is relatively poor due to broad absorption features. The simultaneous determination of several components may be achieved using such calibration techniques. A number of such multivariate data calibration analysis techniques exist. The most often used method for quantitative determination is Partial Least Squares (PLS). A PLS calibration technique has the advantage of allowing automatic detection of samples not coherent within the calibration set (outliers), thus providing a means of controlling the model validity. For example, PLS calibration techniques can solve the overlapped spectrum contributed by the multiple components in the sample analyzed, so that the amounts of the respective components may be obtained with one spectroscopic measurement.

Figure 9:
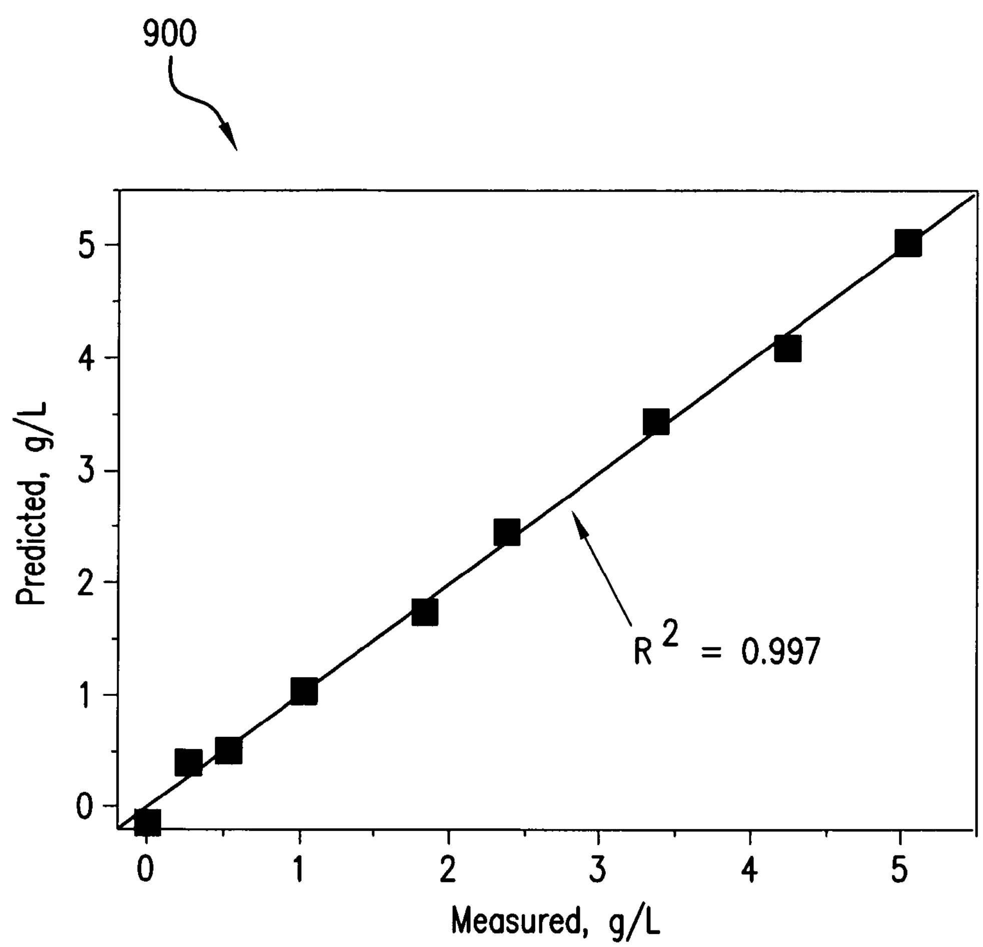
FIG. 9 is graphical plot of a predictive model based on multivariate PLS calibration using relatively low residual sulfide BLOX liquors, versus measured amounts of residual sulfide.

In embodiments of the present invention, a set of sample kraft liquors may be collected, which covers the content variation range of the kraft liquors. ATR-UV/V spectral signals at a wavelength in range from about 190 to about 450 nm (or about 500 nm) may be used for each kraft liquor measurement. A PLS model may be obtained based on the data from the reference methods. Thus, a simultaneous determination of the amount of sulfide, total dissolved solids and effective alkali may be carried out. FIG. 9 is graphical plot, indicated generally as 900, which provides the predicted results for the residual sulfide based on a PLS calibration, and which shows a generally linear relationship with actual measurements. The prediction with such a PLS calibration may be much better than that of the linear models described above.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method comprising the following steps of:

(a) providing spectroscopy results for one or more samples of oxidized black liquor; and (b) determining simultaneously from the sample an amount of sulfide, an amount of total dissolved solids, and an amount of effective alkali present in the one or more samples based on the spectroscopy results of step (a), wherein the spectroscopy results are based on subjecting the one or more samples to attenuated total reflection (ATR) ultraviolet/visible (UV/V) spectroscopy over a wavelength of from about 190 to about 500 nm.

2. The method of claim 1, wherein the spectroscopy results are based on subjecting the one or more samples to attenuated total reflection (ATR) ultraviolet/visible (UV/V) spectroscopy over a wavelength of from about 190 to about 450 nm.

3. The method of claim 1, wherein the one or more samples are a plurality of samples.

4. The method of claim 1, wherein step (b) is carried out using a multivariate calibration technique.

5. The method of claim 4, wherein the multivariate calibration technique is a Partial Least Squares (PLS) regression technique.

6. The method of claim 1, wherein step (b) is carried out using an empirical calibration technique.

7. The method of claim 6, wherein the empirical calibration technique is linear regression calibration technique.

8. The method of claim 1, further comprising the following step: (c) subjecting the one or more samples of oxidized black liquor to attenuated total reflection (ATR) ultraviolet/visible (UVN) spectroscopy over a wavelength of from about 190 to about 500 nm to thereby provide the spectroscopy results of step (a).

9. The method of claim 1, wherein step (b) is carried out using a multivariate calibration technique and an empirical calibration technique.

10. The method of claim 8, wherein step (c) is carried out by passing the one or more samples through an ATR flow cell.

11. A method comprising the following steps of:

(a) providing from a black liquor oxidation system one or more samples each of: (1) oxidized black liquor; and (2) black liquor which may be subjected to black liquor oxidation;

(b) determining simultaneously for each sample an amount of sulfide, an amount of total dissolved solids, and an amount of effective alkali present in each sample based on spectroscopy results for each sample; and (c) monitoring the black liquor oxidation system based on the sulfide amount, the total dissolved solids amount, and the effective alkali amount determined in step (b), wherein the spectroscopy results are based on subjecting the one or more samples to attenuated total reflection (ATR) ultraviolet/visible (UVN) spectroscopy over a wavelength of from about 190 to about 500 nm.

12. The method of claim 11, wherein the spectroscopy results are based on subjecting the one or more samples to attenuated total reflection (ATR) ultraviolet/visible (UV/V) spectroscopy over a wavelength of from about 190 to about 450 nm.

13. The method of claim 11, wherein step (a) provides a plurality of samples of oxidized black liquor and a plurality of samples of black liquor which may be subjected to black liquor oxidation.

14. The method of claim 11, wherein step (b) is carried out using a multivariate calibration technique.

15. The method of claim 14, wherein the multivariate calibration technique is a Partial Least Squares (PLS) regression technique.

16. The method of claim 11, wherein step (b) is carried out using an empirical calibration technique.

17. The method of claim 16, wherein the empirical calibration technique is a linear regression calibration technique.

18. The method of claim 11, wherein step (b) is carried out using a multivariate calibration technique and an empirical calibration technique.

19. The method of claim 11, wherein the black liquor oxidation system of step (a) comprises a first black liquor oxidation stage for converting black liquor to oxidized black liquor, and a second stage black liquor oxidation stage for converting the oxidized black liquor to a further oxidized black liquor, and wherein step (b) is carried out on samples of each of the black liquor, the oxidized black liquor, and the further oxidized black liquor.

20. The method of claim 19, wherein step (b) is carried on a plurality of samples of each of the oxidized black liquor, and the further oxidized black liquor.

21. The method of claim 20, wherein step (b) is carried out on a plurality of samples of the black liquor.

22. The method of claim 11, wherein step (c) further comprises controlling the black liquor oxidization system based on the sulfide amount, the total dissolved solids amount, and the effective alkali amount determined in step (b).

23. The method of claim 22, wherein controlling the black liquor oxidation system during step (c) comprises the steps of: (d) inputting data on the sulfide amount, the total dissolved solids amount, and the effective alkali amount in each sample analyzed from step (b) to a black liquor oxidation control processor; and (e) based on the data inputted, having the black liquor oxidation control processor send signals to control the degree of oxidation of the oxidized black liquor by the black liquor oxidization system.

24. The method of claim 23, wherein the black liquor oxidization system of step (a) comprises at least one oxygen containing source, and wherein the black liquor oxidation control processor sends signals to the at least one oxygen containing source during step (c).

25. The method of claim 24, wherein black liquor oxidation system of step (a) comprises a first black liquor oxidation stage for converting black liquor to oxidized black liquor, and a second stage black liquor oxidation stage for converting the oxidized black liquor to further oxidized black liquor, wherein the at least one oxygen containing source comprises a first oxygen-containing source for converting black liquor to oxidized black liquor in the first black liquor oxidation stage, and a second oxygen-containing source for converting the oxidized black liquor to further oxidized black liquor in the second stage black liquor oxidation stage, and wherein the black liquor oxidation control processor sends signals to the first oxygen containing source and the second oxygen-containing source during step (c).

26. The method of claim 24 wherein the at least one oxygen-containing source of step (a) comprises air or oxygen.

27. The method of claim 24, wherein the black liquor comprises a sulfide amount of at least about 13 g/L, a total dissolved solids amount of up to about 50%, and an effective alkali amount of at least about 6.5 g/L, and wherein the black liquor oxidation system is controlled during step (c) to provide oxidized black liquor comprising a sulfide amount of up to about 1.7 g/L, a total dissolved solids amount of up to about 70%, and an effective alkali amount of up to about 50 g/L.

28. The method of claim 27, wherein the black liquor oxidation system is controlled during step (c) to provide oxidized black liquor comprising a sulfide amount of up to about 0.1 g/L, a total dissolved solids amount in the range of from about 40 to about 55%, and an effective alkali amount of up to about 25 g/L.

29. The method of claim 11, wherein each sample is cooled to a temperature in the range of from about 25° to about 70° C. before carrying out step (b).

30. The method of claim 29, wherein each sample is cooled to a temperature in the range of from about 50° to about 70° C. before carrying out step (b).

31. The method of claim 29, wherein step (b) is carried out for each sample at a temperature which varies by no more than about ±5° C.

32. The method of claim 31, wherein step (b) is carried out for each sample at a temperature which varies by no more than about ±1° C.

33. The method of claim 11, wherein step (b) is carried out by passing the samples obtained directly through an ATR flow cell.

34. The method of claim 11, further comprising the following step: (d) subjecting the one or more samples to attenuated total reflection (ATR) ultraviolet/visible (UV/V) spectroscopy over a wavelength of from about 190 to about 500 nm to thereby provide the spectroscopy results of step (b).

35. The method of claim 34, wherein step (d) is carried out by passing the sample through an ATR flow cell.

36. A system comprising:

a black liquor stream;

at least one black liquor oxidation stage for converting at least a portion of the black liquor stream to an oxidized black liquor stream;

an attenuated total reflection (ATR) ultraviolet/visible (UVN) spectroscopy section for determining simultaneously over a wavelength of from about 190 to about 500 nm an amount of sulfide, an amount of total dissolved solids, and an amount of effective alkali present in samples from the black liquor stream and the oxidized black liquor oxidation stream and for providing data comprising the sulfide amount, the total dissolved solids amount, and the effective alkali amount determined in the samples; and a black liquor oxidation control processor for monitoring and controlling the at least one black liquor oxidation stage based on the data provided from the attenuated total reflection (ATR) ultraviolet/visible (UV/V) spectroscopy section.

37. The system of claim 36, wherein the attenuated total reflection (ATR) ultraviolet/visible (UV/V) spectroscopy section carries out the determination of the sulfide amount, the total dissolved solids amount, and the effective alkali amount over a wavelength of from about 190 to about 450 nm.

38. The system of claim 36, wherein the attenuated total reflection (ATR) ultraviolet/visible (UVN) spectroscopy section carries out the determination of the sulfide amount, the total dissolved solids amount, and the effective alkali amount using a multivariate calibration technique.

39. The system of claim 38, wherein the multivariate calibration technique is a Partial Least Squares (PLS) regression technique.

40. The system of claim 36, wherein the attenuated total reflection (ATR) ultraviolet/visible (UVN) spectroscopy section carries out the determination of the sulfide amount, the total dissolved solids amount, and the effective alkali amount using an empirical calibration technique.

41. The system of claim 40, wherein the empirical calibration technique is a linear regression calibration technique.

42. The system of claim 36, wherein the at least one black liquor oxidation stage comprises a first black liquor oxidation stage for converting the portion of the black liquor stream to the oxidized black liquor stream, and a second stage black liquor oxidation stage for converting at least a portion of the oxidized black liquor stream to a further oxidized black liquor stream.

43. The system of claim 36, wherein the samples are cooled to a temperature in the range of from about 25° to about 70° C. before reaching the attenuated total reflection (ATR) ultraviolet/visible (UVN) spectroscopy section.

44. The system of claim 43, wherein the samples are cooled to a temperature in the range of from about 50° to about 70° C. before reaching the attenuated total reflection (ATR) ultraviolet/visible (UV/V) spectroscopy section.

45. The system of claim 43, wherein the attenuated total reflection (ATR) ultraviolet/visible (UVN) spectroscopy section carries out the determination of the sulfide amount, the total dissolved solids amount, and the effective alkali amount for each sample at a temperature which varies by no more than about ±5° C.

46. The system of claim 45, wherein the attenuated total reflection (ATR) ultraviolet/visible (UVN) spectroscopy section carries out the determination of the sulfide amount, the total dissolved solids amount, and the effective alkali amount for each sample at a temperature which varies by no more than about ±1° C.

47. The system of claim 36, wherein the attenuated total reflection (ATR) ultraviolet/visible (UVN) spectroscopy section comprises an ATR flow cell, wherein the samples are obtained directly from the black liquor stream and the oxidized black liquor stream, and wherein the samples obtained are passed directly through the ATR flow cell.

48. The system of claim 47, wherein the ATR flow cell is periodically purged to remove residues from the ATR flow cell.

49. The system of claim 36, wherein the at least one black liquor oxidization stage comprises at least one oxygen containing source, and wherein the black liquor oxidation control processor sends signals to the at least one oxygen containing source to control oxidization in the at least one black liquor oxidization stage.

50. The system of claim 49, wherein the at least one oxygen-containing source provides air or oxygen to the at least one black liquor oxidation stage.

51. The system of claim 36, wherein the attenuated total reflection (ATR) ultraviolet/visible (UVN) spectroscopy section comprises an ATR sensor which analyzes each sample, a spectrophotometer connected to the ATR sensor which receives light absorbed by the ATR sensor from each analyzed sample and which generates an absorbency spectrum over the wavelength range in the form of spectral data, and a spectral data analyzer which analyzes the spectral data to determine the sulfide amount, the total dissolved solids amount, and the effective alkali amount for each analyzed sample.

52. The system of claim 51, wherein the ATR sensor comprises an ATR flow cell through which each analyzed sample passes, and wherein the spectral data analyzer comprises a computer.

53. The system of claim 36, wherein the black liquor stream comprises a sulfide amount of at least about 13 g/L, a total dissolved solids amount of about 50% or less, and an effective alkali amount of at least about 6.5 g/L, and wherein the black liquor oxidation control processor controls the oxidation and conversion of the portion of the black liquor stream by the at least one black liquor oxidation stage to provide an oxidized black liquor stream comprising a sulfide amount of up to about 1.7 g/L, a total dissolved solids amount of up to about 70%, and an effective alkali amount of up to about 50 g/L.

54. The system of claim 53, wherein the black liquor oxidation control processor controls the oxidation and conversion of the portion of the black liquor stream by the at least one black liquor oxidation stage to provide an oxidized black liquor stream comprising a sulfide amount of up to about 0.1 g/L, a total dissolved solids amount in the range of from about 40 to about 55%, and an effective alkali amount of up to about 25 g/L.

* * * * *